United States Patent [19]

Zöchbauer

[11] 4,326,807

[45] Apr. 27, 1982

[54] PHOTOELECTRIC GAS ANALYZER

[75] Inventor: Michael Zöchbauer, Oberursel, Fed. Rep. of Germany

[73] Assignee: Hartmann & Braun Aktiengesellschaft, Frankfurt am Main, Fed. Rep. of Germany

[21] Appl. No.: 189,620

[22] Filed: Sep. 22, 1980

[30] Foreign Application Priority Data

Oct. 1, 1979 [DE] Fed. Rep. of Germany ....... 2939735

[51] Int. Cl.³ ............................................. G01J 3/48
[52] U.S. Cl. .................... 356/418; 250/343; 356/51
[58] Field of Search ................. 356/51, 418; 250/339, 250/343

[56] References Cited

U.S. PATENT DOCUMENTS 3,694,086 9/1972 May ........................................ 356/51
3,893,770 7/1975 Takami et al. ................... 356/51 X
3,947,685 3/1976 Meinel ................................ 250/343
4,176,963 12/1979 Fabinski et al. ..................... 356/418

OTHER PUBLICATIONS

Lefers, *Analytical Chemistry*, vol. 52, No. 9, Aug. 1980, pp. 1424–1426.

Primary Examiner—F. L. Evans
Attorney, Agent, or Firm—Smyth, Pavitt, Siegemund & Martella

[57] ABSTRACT

An analyzer for measuring the combined NO and $NO_2$ concentrations includes a hollow cathode lamp with nitrogen/oxygen filling emitting radiation which is alternatingly passed through two narrow-band interference filters, one having a transmission range clearly outside any NO absorption bands and its $NO_2$ absorption equals the difference of the absorption coefficients for NO and $NO_2$ in the transmission band of the other filter. These two beams pass through a measuring gas cell and are photoelectrically detected for further processing.

8 Claims, 2 Drawing Figures

PHOTOELECTRIC GAS ANALYZER

BACKGROUND OF THE INVENTION

The present invention relates to photoelectric gas analysis under utilization of the specific absorption of radiation by a gas upon being traversed by such radiation.

U.S. Pat. No. 3,694,086 is representative of this field of art; it describes a correlation spectrometer for measuring the concentration of certain gases such as $SO_2$, NO, $NO_2$, and others. The equipment disclosed in that patent includes a source of ultraviolet light. A transducer introduces cyclically a dual-filter into the light path so that, alternatingly, two wavelengths are transmitted and pass through the gas; one of the wavelengths is an absorption line of the component to be detected, the other wavelength is not. The intensities of the radiation at the two wavelengths are detected photoelectrically and processed to obtain a measuring result.

U.S. Pat. No. 3,947,685 discloses measuring the NO content in a carrier using a particular hollow cathode tube emitting radiation which is alternatingly intercepted by two cuvettes, one containing NO, the other one air. Thus, the filter containing NO also preabsorbs some of the radiation to which the component to be detected is specifically responsive. Moreover, the source of radiation for this equipment is specifically constructed to emit radiation by exciting NO molecules; it is, thus, specific as to the gas concentration to be detected. See also U.S. Pat. No. 4,176,963.

DESCRIPTION OF THE INVENTION

It is an object of the present invention to provide a new and improved photoelectric gas analyzer by means of which one can determine directly the sum of the NO and $NO_2$ concentrations in a gas mixture.

One could, of course, simply measure the two components separately by means of duplicated equipment as per U.S. Pat. No. 3,694,086 and form the sum from the components; or one could change the one component chemically into the other one by chemical reaction. Either approach is obviously quite expensive. Moreover, running such chemical reactions incurs additional maintenance expenses, and the power consumption is disproportionally high. Furthermore, it was found to be difficult, generally, to eliminate the effect that other gas components may have on the measuring result.

It is, therefore, an object of the invention to find a different approach for measuring the sum of the NO and $NO_2$ concentrations in a carrier gas.

It is a specific object of the present invention to improve photoelectric gas analyzers using a source of radiation, a cell containing or being passed through by a gas whose NO and $NO_2$ concentration is to be measured, and photoelectric detection means.

In accordance with the preferred embodiment of the present invention, it is suggested to provide two narrowband, preferably adjustable, interference filters for generating two radiation components which traverse the cell, whereby the transmission band of one of the interference filters passes radiation outside an NO absorption band, and the effective absorption coefficient for $NO_2$ in that band is equal to the difference of the absorption coefficients for $NO_2$ and NO in the transmission band of the other filter. The source of radiation is to be of the kind that emits radiation in an emission band of NO molecules. The ratio of the detected intensities in the transmission bands of the two filters, after having passed through the measuring cell, is directly indicative of the combined NO and $NO_2$ concentrations. Particular adjustment (e.g., tilting) of the filters permits, moreover, an elimination of one other interfering component, e.g., $SO_2$, from the measuring output.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

Proceeding now to the detailed description of the drawings, FIG. 1 illustrates a hollow cathode lamp 1 of a known variety, emitting a beam of radiation rich in NO lines. The beam is intercepted by a rotating disk 2 having apertures 8 and 9. Interference filters 10 and 11 are respectively mounted on the windows in pivotal fashion; i.e., they can be oriented at less than a right angle to the beam of radiation permitted to pass the respective aperture. Thus, diaphragm disk 2 produces alternatingly two beams which propagate intermittently along the same path; but each one has a different frequency spectrum in accordance with the transmission bands of the two filters 10 and 11.

Figure 1:
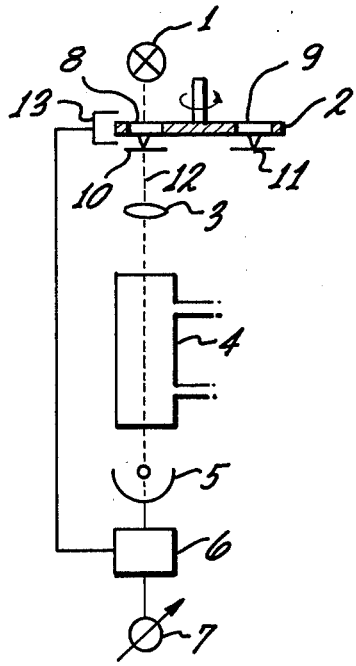
FIG. 1 is a schematic illustration of a gas analyzer in accordance with the preferred embodiment of the invention.

Radiation permitted to pass is collimated by a lens or lens system 3 and directed as a parallel beam (two beams) into and through a measuring cuvette or cell 4 having gas inlet and outlet ducts for being flown through by the gas to be analyzed. This gas consists, for example, of waste gas, exhaust fumes, or the like. Radiation permitted to pass through and exiting from cell 4 is detected by a photoelectric detector 5 providing an electrical signal to a processing stage 6 which causes an instrument 7 to indicate the measuring result.

The purpose of the device is to indicate, in particular, the total concentration of NO and $NO_2$ combined. The lamp 1 is filled with nitrogen and oxygen at a low pressure and is operated as described in U.S. Pat. No. 3,947,685 under utilization of a small discharge current. Thus, the radiation emitted is particularly rich in NO emission bands.

The two filters 10 and 11 have respectively transmissive characteristics, as indicated by the curves $T_M$ and $T_R$. The pivotal arrangement of the filters permits their adjustment to the desired filter range; i.e., one can shift the transmission band with regard to its frequency by such pivotal adjustment in order to obtain the exact spectral characteristics of the filters for the desired purpose and function to be described more fully below.

Reference numeral 13 refers to a (magnetic, photoelectric, or the like) pickup which provides signals indicative in phase to the relative dispostion of the rotating filters. This synchronization signal is used to synchronize the processing stage 6. Particularly, the pickup 13 identifies the beam as a measuring beam, when the filter 10 is controlling, and as a reference beam when the filter 11 is controlling. Filter 10 can, thus, be termed the measuring filter; the radiation it transmits is characterized in FIG. 2 by transmission band $T_M$, while filter 11 transmits a reference beam of frequency in band $T_R$.

Let $I_{M0}$ and $I_{R0}$ be the intensities of the measuring and reference beam respectively prior to passage through cell 4, and $I_M$ and $I_R$ be respectively the intensities after passage through cell 4, one can then define frequency-specific radiation transmission of cell 4 as the ratios $I_M/I_{M0}$ and $I_R/I_{R0}$.

Figure 2:
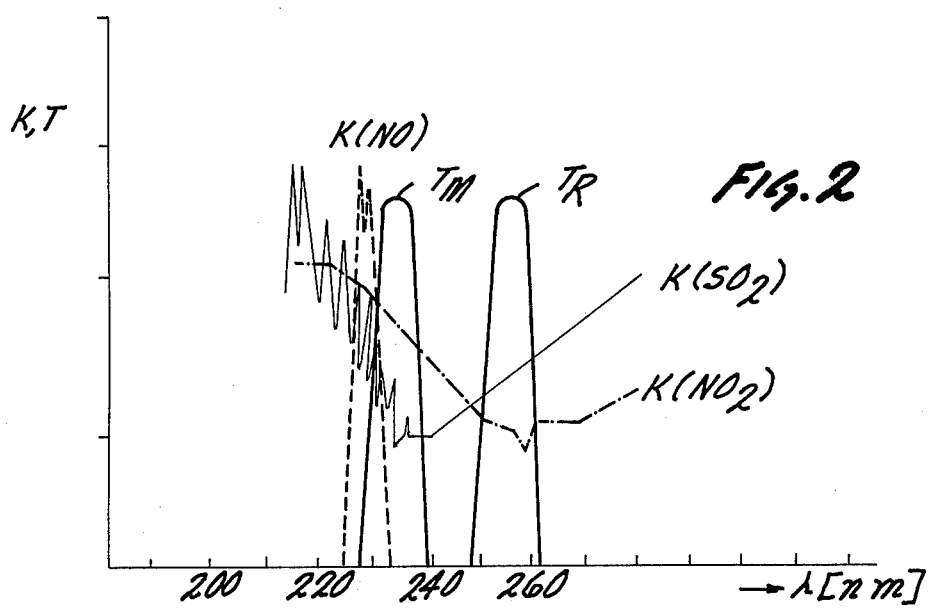
FIG. 2 is a diagram in which relevant absorption coefficients and filter transmission ranges are superimposed and plotted against wavelengths, for practicing the preferred embodiment in accordance with the best mode of the invention under utilization of the analyzer shown in FIG. 1.

FIG. 2 shows further, on a relative scale, absorption coefficients K for NO, NO$_2$, and SO$_2$. It can readily be seen that the coefficient K (NO) is zero in reference band $T_R$ of filter 11. Thus, NO will not absorb the reference beam. In the following, certain terms will be used. $c^{NO}$, $c^{SO2}$, and $c^{NO2}$ are respectively the concentrations of NO, SO$_2$, and NO$_2$ in the gas flowing through cell 4. $K_R^{NO}$, $K_M^{SO2}$, and so forth, are the specific absorption coefficient values for NO, SO$_2$, and so forth, in the reference band (index R) or in the measuring band (index M). Let l be the length of cell 4, then the Lambert-Beer law establishes the following equation:

$$(I_M)/(I_{M0}) = \exp[-l(c^{NO}K_M^{NO} + c^{NO2}K_M^{NO2} + c^{SO2}K_M^{SO2})] \quad (1)$$

$$(I_R)/(I_{R0}) = \exp[-l(c^{NO}K_R^{NO} + c^{NO2}K_R^{NO2} + c^{SO2}K_R^{SO2})] \quad (2)$$

The circuit 6 receives alternatingly signals which are proportional to $I_M$ and $I_R$. The circuit forms a quantity A, given by $$A = 1 - (I_M/I_R)$$

Using the relation of the Lambert-Beer law above, one will find that A represents the following equation:

$$A = 1 - (I_{M0})/(I_{R0})\exp\{-l[c^{NO}(K_M^{NO} - K_R^{NO}) + c^{NO2}(K_m^{NO2} - K_R^{NO2}) + c^{SO2}(K_M^{SO2} - K_R^{SO2})]\} \quad (4)$$

One can, of course, measure the values $I_{M0}$ and $I_{R0}$ separately, eliminating thereby any variations in the hollow cathode lamp (see U.S. Pat. No. 4,176,963). If, on the other hand, these variations do not occur or are, in effect, insignificant, the value $I_{M0}/I_{R0}$ is a constant and can be dealt with by calibration.

In order to actually measure the sum of the concentrations of NO and NO$_2$($c^{NO}+c^{NO2}$), one must establish the relation $$K_M^{NO} - K_R^{NO} = K_M^{NO2} - K_R^{NO2} \quad (5)$$

Since actually $K_R^{NO} = 0$, the relation is reduced to $$K_M^{NO} = K_M^{NO2} - K_R^{NO2} \quad (6)$$

This means that the filters have to be adjusted to that absorption coefficient for NO of the measuring beam (filter 10, $T_M$) is to be equal to the absorption coefficients for NO$_2$ in the two bands. The equation can be written also as $$K_R^{NO2} = K_M^{NO2} - K_M^{NO} \quad (6a)$$

which means that the absorption coefficient for NO$_2$ of the reference beam band (filter 11, $T_R$) is to be equal to the difference of absorption coefficients in the measuring band (filter 11, $T_M$) for NO$_2$ and NO. A third version can be analogously interpreted.

Tilting of filter 10 establishes this relation. As long as this is the only condition to be met, both filters can be adjusted for fine-tuning. However, SO$_2$ may be present, and the equipment offers the possibility to eliminate any interfering effect on that account. Filter 11 is tilted into a position to establish $$K_M^{SO2} = K_R^{SO2} \quad (7)$$

A change here may slightly offset the condition (6) or (6a), but both relations (6) and (7) can readily be approximated. Thus the relation (4) is reduced to $$A = 1 - \exp\{-lK_M^{NO}(c^{NO} + c^{NO2})\}$$

Consequently, signal A is directly related to the sum $c^{NO} + c^{NO2}$ to be detected; the SO$_2$ concentration does not interfer with that result. One can also say that the ratio of the measured intensities of the two beams equals the exponential function of the sum of the desired concentrations, multiplied by an instrument parameter l and by the absorption coefficient for NO in the narrow measuring band $T_M$. Therefore, circuit 6 merely needs to form the ratio of the alternatingly arriving signals representing $I_M$ and $I_R$ and, either by exponential signal processing or just calibration on an exponential scale, $c^{NO} + c^{NO2}$ can be directly arrived at and indicated.

The invention is not limited to the embodiments described above; but all changes and modifications thereof, not constituting departures from the spirit and scope of the invention, are intended to be included.

I claim:

1. Photoelectric gas analyzer, for detecting the sum of the concentrations of NO and NO$_2$ in a gas and having a source of radiation, a cell containing the gas and disposed to receive radiation from the source, photoelectric detection means for receiving the radiation having passed through the cell, and circuit means connected to the detection means, the improvement comprising:
   means for establishing two radiation beams traversing the same cell, and including
   (i) a first interference filter adjusted to have a first transmission range outside any absorption band for NO to, thereby, establish one of the beams; and
   (ii) a second interference filter, establishing the other one of the beams and being adjusted to have a second transmission range in an overlapping absorption region for NO and NO$_2$ in such a way that the effective absorption coefficient of NO$_2$ in the first transmission range of the first filter equals the difference of the absorption coefficients of NO$_2$ and NO in said second range; and
   the source being a hollow cathode lamp filled with nitrogen and oxygen, the photoelectric detector means being responsive to the two beams and the circuit means constructed to provide an indication representing the sum of the concentrations of NO and NO$_2$.

2. Analyzer as in claim 1, the filters being tiltably mounted.

3. Analyzer as in claim 1 or 2, wherein the two beams traverse the same path, the filters being mounted for rotation to alternately intercept the radiation from the source.

4. Photoelectric analyzer as in claim 1, wherein the first interference filter is adjusted so that the absorption for $SO_2$ is at least approximately the same as for both transmission bands.

5. Photoelectric gas analyzer for detecting the sum of the concentrations of two different components in a gas, comprising:
   a source of radiation;
   first filter means disposed in a path of said radiation and having a first transmission band outside any absorption band of a first one of said components, thereby establishing a first beam;
   second filter means disposed in a path of said radiation and having a second transmission band in an overlapping absorption range for the two components in such a way that the effective absorption coefficient of the second component in the first transmission band equals the difference of the absorption coefficients for the two components in the second range, thereby establishing a second beam;
   a measuring cell disposed to be passed through by the first and second beams;
   photoelectric detector means responsive to the first and second beams following passage through the measuring cell; and
   circuit means for combining outputs produced by the detector means.

6. Analyzer as in claim 5, wherein the first and second beams are alternatingly produced and pass through an identical path through the cell.

7. Analyzer as in claim 5 or 6, wherein the filter means are adjustable, narrow transmission band interference filters.

8. Photoelectric analyzer for detecting the sum of the concentrations of two different components in a gas, comprising:
   a source of radiation;
   first and second filter means disposed to receive said radiation and respectively providing two beams, the filter means having different transmission bands in such a way that the difference in absorption coefficients of a first one of the components in the two transmission bands equals the difference in absorption coefficients of a second one of the components in the two transmission bands;
   a measuring cell disposed to be passed through by the first and second beams;
   photoelectric detector means responsive to the first and second beams following passage through the measuring cell; and
   circuit means for combining outputs produced by the detector means.

* * * * *